US008979817B2

(12) United States Patent
Chung et al.

(10) Patent No.: US 8,979,817 B2
(45) Date of Patent: Mar. 17, 2015

(54) MULTI-CHAMBER CONTAINER WITH SEAL BREACH DETECTION

(75) Inventors: Terry Chung, Kildeer, IL (US); William Cork, Lake Bluff, IL (US); Kwang Suk Kim, Palatine, IL (US)

(73) Assignee: Fenwal, Inc., Lake Zurich, IL (US)

( * ) Notice: Subject to any disclaimer, the term of this patent is extended or adjusted under 35 U.S.C. 154(b) by 41 days.

(21) Appl. No.: 13/548,349

(22) Filed: Jul. 13, 2012

(65) Prior Publication Data

US 2013/0018353 A1 Jan. 17, 2013

Related U.S. Application Data

(60) Provisional application No. 61/507,712, filed on Jul. 14, 2011.

(51) Int. Cl.

| | |
|---|---|
| ***A61M 19/00*** | (2006.01) |
| ***A61J 1/20*** | (2006.01) |
| *A61J 1/18* | (2006.01) |
| *A61J 1/10* | (2006.01) |

(52) U.S. Cl.

CPC . *A61J 1/2093* (2013.01); *A61J 1/18* (2013.01); *A61J 1/10* (2013.01); *A61J 2001/2024* (2013.01)

USPC .......... 604/410; 604/408

(58) Field of Classification Search

CPC .......... A61J 1/18; A61J 1/10; A61J 1/2093; A61J 2001/202; A61J 2001/2024

USPC .......... 604/408, 410

See application file for complete search history.

(56) References Cited

U.S. PATENT DOCUMENTS

| | | | | |
|---|---|---|---|---|
| 4,507,114 | A * | 3/1985 | Bohman et al. | 604/111 |
| 6,398,771 | B1 * | 6/2002 | Gustafsson et al. | 604/410 |
| 6,726,671 | B2 * | 4/2004 | Dumont et al. | 604/408 |
| 6,764,481 | B1 * | 7/2004 | Inada et al. | 604/408 |
| 7,585,428 | B1 * | 9/2009 | Marshall et al. | 252/62.2 |
| 2007/0029001 | A1 * | 2/2007 | Trouilly et al. | 141/114 |
| 2007/0123836 | A1 * | 5/2007 | Fukushima et al. | 604/410 |
| 2013/0168279 | A1 * | 7/2013 | Sandford | 206/438 |

* cited by examiner

*Primary Examiner* — Leslie Deak

(74) *Attorney, Agent, or Firm* — Cook Alex Ltd.

(57) ABSTRACT

A container having multiple compartments formed by frangible seals in the interior chamber of the container is disclosed. The container comprises an indicator adapted to provide an indication that a seal breach between the chambers has occurred. Methods of forming a container having a seal breach detection indicator are also disclosed.

29 Claims, 4 Drawing Sheets

MULTI-CHAMBER CONTAINER WITH SEAL BREACH DETECTION

REFERENCE TO OTHER APPLICATION

This application claims the benefit of U.S. Provisional Patent Application Ser. No. 61/507,712, filed Jul. 14, 2011, which is incorporated by reference in its entirety.

BACKGROUND OF THE DISCLOSURE

The present disclosure relates generally to the field of containers such as containers for medical and/or biological solutions. The present disclosure relates specifically to a multi-chamber container configured to provide an indication that a seal breach between chambers has occurred.

Certain solutions (e.g., medical solutions) are formed by mixing or combining together two or more components prior to use. For some such solutions, it is desirable keep the solution components separate during various steps of processing and/or separate until ready to be used. The solution components may be combined once the need for the components to be separated has passed and/or before use of the solution. Solution components may be separated for a variety of reasons including stability, to ensure compatibility and to prevent premature reaction between solution components. Further, such solutions may be stored in containers having multiple compartments separated by a peelable or frangible seal. In some applications, each compartment of the container may hold a different solution component, and when mixing of the solution components is desired, the seal between the separate compartments is broken allowing the solution components to mix.

SUMMARY

In one aspect, the present disclosure is directed to a container comprising opposed first and second sheets sealed along a peripheral edge to define an interior chamber comprising a top edge, a bottom edge and first and second opposing lateral edges. There are at least first and second frangible seals located in the interior chamber, forming separate first, second and third compartments in the interior chamber. The third compartment is located between the first and second compartments, the third compartment being defined by the first and second frangible seals and at least a portion of the top and bottom peripheral edges. The third compartment comprises an indicator adapted to detect premature breach of one or both of the at least first and second frangible seals.

In another aspect, the present disclosure is directed to a method of forming a container having a seal breach detection indicator. The method comprises the steps of sealing first and second opposing sheets at their peripheral edges to form an interior chamber comprising a top edge, a bottom edge and first and second opposing lateral edges and forming at least first and second frangible seals between the opposing sheets to define first, second and third compartments in the interior chamber. The third compartment is located between the first and second compartments and is defined by the at least first and second frangible seals and at least a portion of the top and bottom peripheral edges. The method further comprises filling the first chamber with a first solution and filling the second chamber with a second solution and detecting the presence of at least one of the first and second solutions in the third chamber to determine premature breach of at least one of the first and second frangible seals.

DETAILED DESCRIPTION

The present disclosure provides a general description of multi-chamber containers configured to provide an indication that a seal breach between chambers has occurred as well as methods for making such containers. The embodiments disclosed herein also provide a general description of the various components that may be contained in the multiple chambers. These embodiments are only exemplary, and may be embodied in various forms. Therefore, specific details disclosed herein are not to be interpreted as limiting the subject matter of the invention which is set forth in the accompanying claims.

In one embodiment, a multi-chamber container, in accordance with the present disclosure, includes at least one frangible seal in the container interior chamber, thus forming at least two chambers in the interior chamber. More preferably however, the multi-chamber container includes at least two frangible seals, thus forming first, second and third chambers in the container interior chamber. It is also contemplated that the multi-chamber container may include more than two frangible seals, such that the container interior chamber may be divided into more than three compartments. In other words, the multi-chamber container is not limited to a particular number of frangible seals and/or compartments in the interior of the container. In addition, the frangible seals and multiple compartments are not limited to any particular shape, size or configuration. In one example, the frangible seals may be substantially linear, curved, zig-zag, serpentine or the like. It will also be appreciated that the compartments may also have various shapes, including, but not limited to rectangular, square, triangular, circular, or any combination thereof.

The multi-chamber container may be used to hold any material for which it is desirable to provide a separation between two or more materials. While one or more of the multiple chambers may contain medical or therapeutic solutions (or parts of solutions) for the storage and/or preservation of blood components, one or more of the other multiple chambers may contain blood or the blood components themselves. Of course, it is also contemplated that one or more of the multiple chambers may contain other materials in various forms, including solids, gels, liquids, powders and the like, or combinations thereof.

Figure 1:
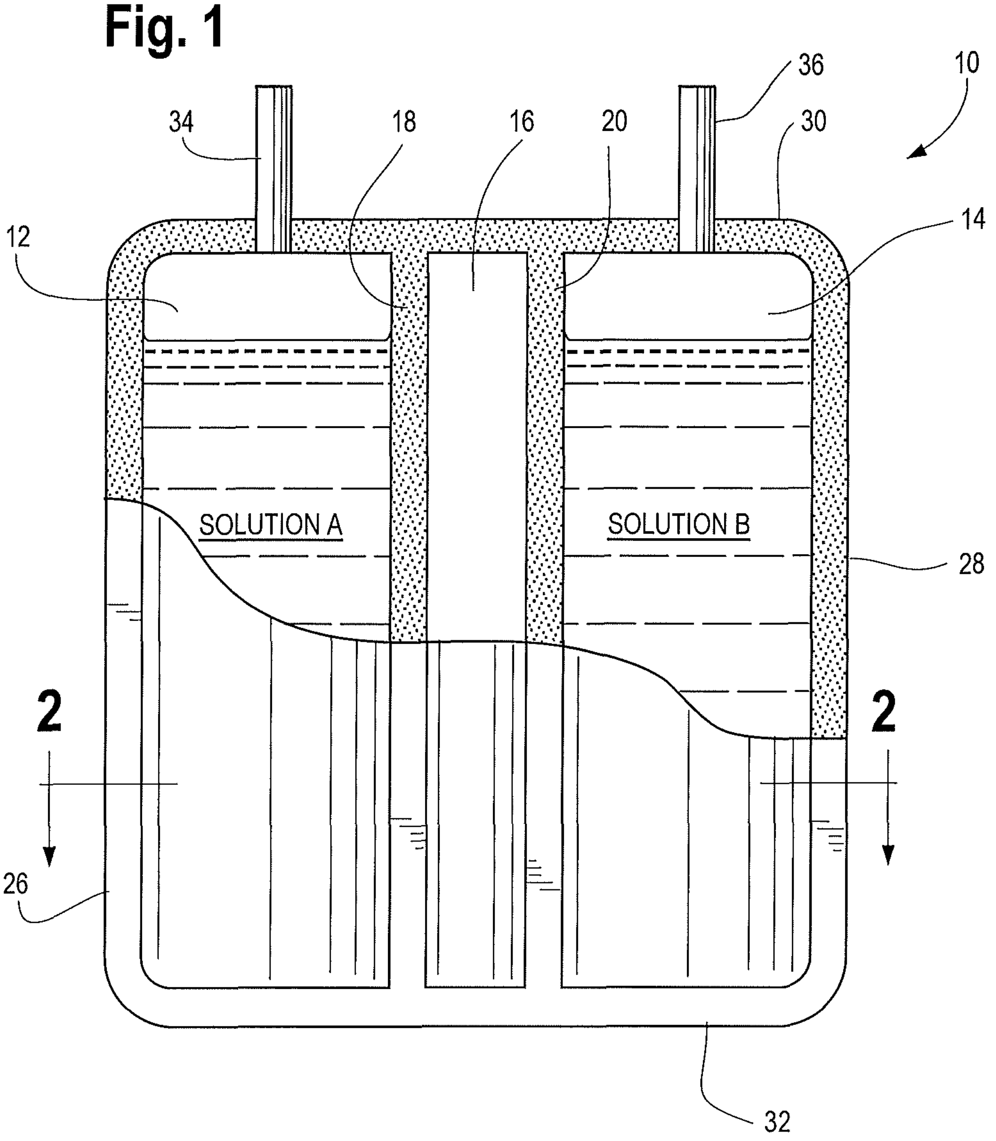
FIG. 1 is a front view of a multi-chamber container according to an exemplary embodiment.
Figure 2:
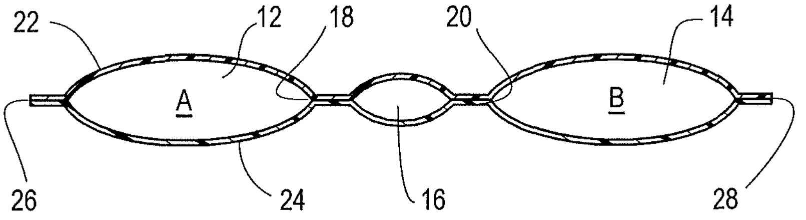
FIG. 2 is a cross-sectional view of the multi-chamber container of FIG. 2.
Figure 3:
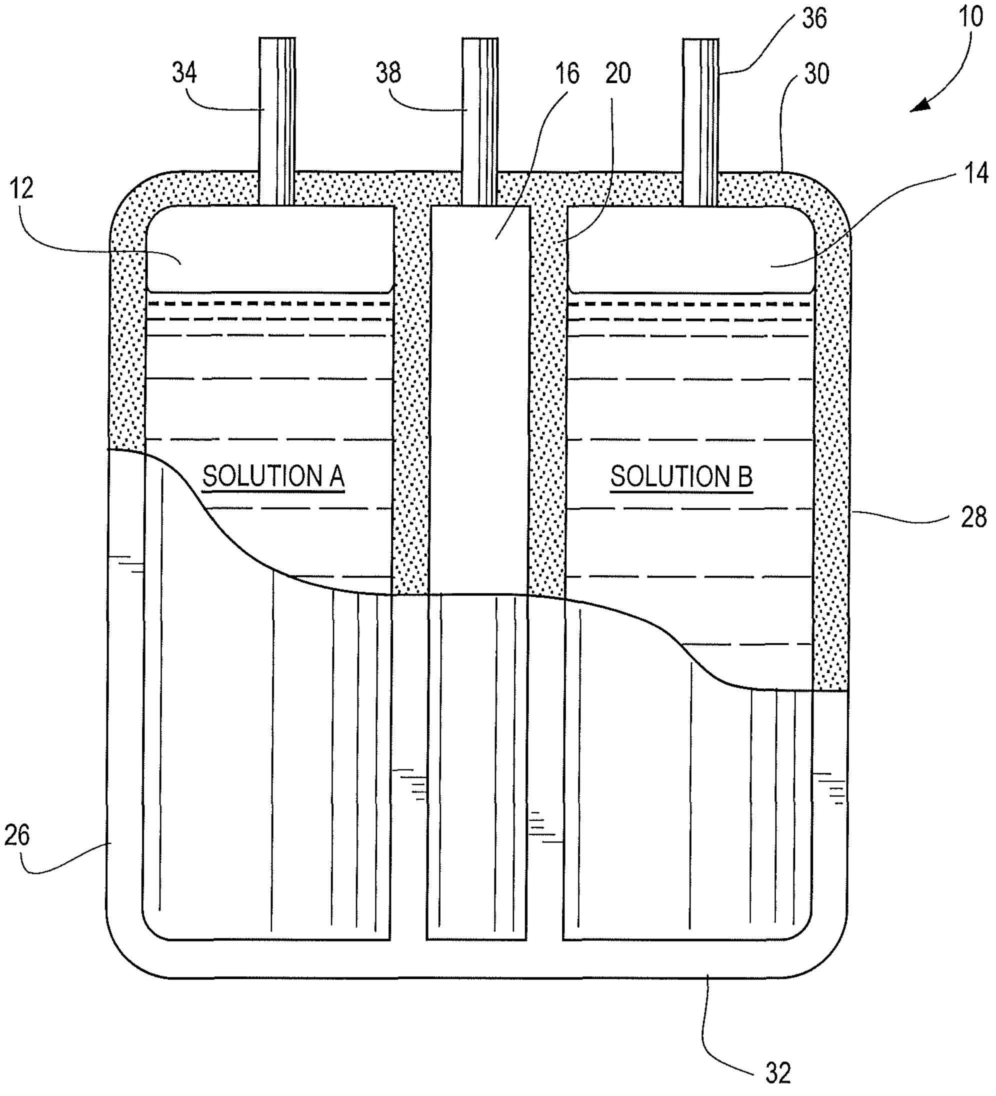
FIG. 3 is a front view of a multi-chamber container according to another exemplary embodiment.

More specifically, referring to FIGS. 1-3, a multiple chamber or multiple compartment container 10 is shown according to an exemplary embodiment. In the embodiment shown, container 10 includes a first chamber, shown as first compartment 12, and a second chamber, shown as second compartment 14, that provide for separate storage of solutions, substances, components, etc., within container 10. Container 10 also includes a third chamber, shown as third compartment 16, located between first compartment 12 and second compartment 14. In the embodiment shown in FIGS. 1-3, third compartment 16 separates compartment 12 from compartment 14 such that fluid must pass through compartment 16 in order to move between compartments 12 and 14.

In the embodiment of FIGS. 1-3, container 10 includes a first frangible seal 18 and a second frangible seal 20. Seal 18 is located between first compartment 12 and third compartment 16, and seal 20 is located between the second compartment 14 and the third compartment 16. Seals 18 and 20 hermetically seal the interfaces between third compartment 16 and first and second compartments 12 and 14, respectively. Seals 18 and 20, when unbroken, prevent fluid from flowing out of first and second compartments 12 and 14 past seals 18 and 20, respectively.

As shown in the exemplary embodiment of FIG. 1, first compartment 12 holds a first material, shown as solution A, and second compartment 14 holds a second material, shown as solution B. It may be desirable for solutions A and B to be separated for a variety of reasons including increasing stability of the solutions, preventing unwanted and/or premature reactions between solutions, ensuring compatibility of the solutions at the time of use, etc. In the embodiment shown, compartment 16 does not include a solution and is substantially empty or devoid of liquid material, and as explained below, compartment 16 functions to provide an indication of whether seals 18 and 20 have been breached.

Referring to FIG. 2, a cross-sectional view of container 10 taken along line 2-2 in FIG. 1 is shown. As shown in FIG. 2, container 10 is shown as a bag-type container formed from two sheets of flexible (e.g., a plastic or polymer) material, shown as first sheet 22 and second sheet 24. To form container 10 the left lateral edges of sheets 22 and 24 are sealed together by seal 26, and the right lateral edge of sheets 22 and 24 are sealed together by seal 28. Referring back to FIG. 1, the upper edges of sheets 22 and 24 are sealed together by upper seal 30, and the lower edges of sheets 22 and 24 are sealed together by lower seal 32. In contrast to frangible seals 18 and 20, seals 26, 28, 30 and 32 are non-frangible seals and form a tight bond that forms a hermetic seal around the periphery of container 10. Together, outer seals 26, 28, 30 and 32 form a peripheral or outer seal of container 10. In one embodiment, container 10 may be formed from a single sheet of flexible material folded back on its self such that one of the lateral edges of the container is defined by the fold and the other lateral edges of the container are defined by seals between adjacent sections of the folded sheet of material.

As shown in FIG. 2, the chamber of first compartment 12 is defined by the inner surfaces of portions of sheets 22 and 24. As shown in FIG. 1, the left lateral edge of first compartment 12 is defined by seal 26, and the right lateral edge of first compartment 12 is defined by frangible seal 18. The upper edge of first compartment 12 is defined by the portion of upper seal 30 between seal 26 and frangible seal 18, and the lower edge of first compartment 12 is defined by the portion of lower seal 32 between seal 26 and frangible seal 18. In one embodiment, the outer edge of compartment 12 is defined by the portion of the outer seal of container 10 on the opposite side of frangible seal 18 from third compartment 16 and the inner edge of compartment 12 is defined by seal 18.

As shown in FIG. 2, the chamber of second compartment 14 is defined by the inner surfaces of portions of sheets 22 and 24. As shown in FIG. 1, the right lateral edge of second compartment 14 is defined by seal 28, and the left lateral edge of second compartment 12 is defined by frangible seal 20. The upper edge of second compartment 14 is defined by the portion of upper seal 30 between seal 28 and frangible seal 20, and the lower edge of second compartment 14 is defined by the portion of lower seal 32 between seal 28 and frangible seal 20. In one embodiment, the outer edge of compartment 14 is defined by the portion of the outer seal of container 10 on the opposite side of frangible seal 20 from third compartment 16 and the inner edge of compartment 14 is defined by seal 20.

As further shown in FIG. 2, the cavity of third compartment 16 is defined by the inner surfaces of portions of sheets 22 and 24. As shown in FIG. 1, the left and right lateral edges of third compartment 16 are defined by frangible seals 18 and 20, respectively. The upper edge of third compartment 16 is defined by the portion of upper seal 30 between frangible seals 18 and 20, and the lower edge of third compartment 16 is defined by the portion of lower seal 32 between frangible seals 18 and 20. In the embodiment shown in FIGS. 1 and 3, compartments 12, 14 and 16 are substantially rectangular compartments in which frangible seals 18 and 20 are parallel to the left and right lateral edges of container 10. In other embodiments, container 10 and compartments 12, 14 and 16 may be other shapes as desired for a particular application.

When mixing of solutions A and B is desired, frangible seals 18 and 20 are broken allowing solutions A and B to mix within container 10. In the embodiment shown, seals 18 and 20 are peelable seals that can be broken with the application appropriate force, and seals 18 and 20 are configured such that the force that opens seals 18 and 20 will not break the outer peripheral seal of container 10.

As noted above, in one embodiment, while frangible seals 18 and 20 are intact, third compartment 16 is substantially devoid of liquid. Thus, compartment 16 acts to provide an indication of whether either seal 18 or seal 20 has been broken or breached by providing an inspection area that will show if fluid from compartments 12 or 14 is present in compartment 16. For example, if upon inspection, liquid is discovered within compartment 16, this indicates that seal 18 and/or seal 20 has been breached, and appropriate action can be taken based on the detection. For example, in one embodiment, container 10 may be discarded if compartment 16 indicates that a premature or unintentional breach of one or more of the seals has occurred.

In one embodiment, inspection of compartment 16 for the presence of fluid may occur via visual inspection by a user (e.g., a worker at a manufacturing or filling facility for container 10, a health care professional administering the contents of container 10 to a patient, etc.). In another embodiment, inspection of compartment 16 for the presence of fluid may occur via a device or system configured to detect the presence fluid within compartment 16. For example, the device may be a machine vision system configured to detect diffusion of light caused by the presence of fluid droplets. In another embodiment, the device may be an ultrasound based device configured to detect propagation of sound waves through liquid droplets.

In various embodiments, container 10 may be configured to facilitate detection of liquid within compartment 16. For example, the portion of the material of container 10 located between frangible seals 18 and 20 may be transparent, forming a window that allows the user to see into compartment 16. In one such embodiment, container 10 may be made from a polymer or plastic material, and the portion of the polymer or plastic material that forms compartment 16 may be a transparent polymer material that allows the user/machine to easily see through the material of compartment 16. In one such embodiment, the portion of the polymer or plastic material of container 10 that forms compartment 16 may have a smooth outer finish to increase light transmission through compartment 16. In one such embodiment, the material of compartment 16 may have a smooth outer finish such that compartment 16 is transparent, and the material of compartments 12 and 14 is textured or "frosted" such that the material of compartments 12 and 14 is translucent or opaque.

In some embodiments, compartment 16 may include one or more indicator devices or materials configured to provide an indication that seals 18 and/or 20 have been prematurely breached and that unintended mixture of solutions A and B has occurred. In one such embodiment, compartment 16 may include an indicator material that provides an indication (e.g., a color change) that fluid has entered compartment 16, and if the breach has occurred at an unintended time (e.g., during processing, shipping, storage, etc. of container 10), container 10, with a premature breach of seal 18 or 20, can be disposed of prior to use of the solution.

In various embodiments, the indicator material can be any material capable of providing an indication that either seal 18 or 20 has been breached. For example, the indicator material may change color based on the presence of liquid, based on the pH of solutions A and B, the ion concentration of solutions A and B, the presence of specific molecules/chemicals of solutions A and B, etc. The indicator material may be any suitable type of material including, a solid material, a fluid material (e.g., a liquid, a liquid solution, a gas, a gaseous solution, etc.), a powdered material, etc. In one embodiment, the indicator material may provide a first indication specific to the presence of solution A and a second indication specific to the presence of solution B allowing the user to tell whether seal 18, seal 20 or both seals 18 and 20 have been breached. In one such embodiment, compartment 16 may include a first indicator material responsive to the presence of solution A and a second indicator material responsive to solution B. The first indicator material and/or the second indicator material may be the same or they may be different, and may also be responsive to the presence of both solutions A and B.

In some embodiments, the indicator material or materials may be located in areas of container 10 other than the chamber within compartment 16. For example, the indicator material may be incorporated into the polymer material that forms compartment 16. In this embodiment, incorporation of the indicator material within the matrix of the polymer material may prevent the indicator material from mixing with the solution following intentional breach of seals 18 and 20. In another embodiment, an indicator material may be located within seals 18 and 20, and the indicator may provide a localized indication that fluid has traversed seal 18 and 20. In one such embodiment, the indicator material may be a strip of indicator material embedded within seals 18 and 20 that extends a portion of and/or the entire length of seals 18 and 20.

Container 10 includes one or more ports, shown as ports 34 and 36, in FIG. 1. Ports 34 and 36 traverse the outer peripheral seal of container 10 adjacent to compartments 12 and 14. Ports 34 and 36 provide for fluid communication with compartments 12 and 14, respectively. As such, ports 34 and 36 provide an access point allowing fluids to be moved into or out of compartments 12 and 14, and ports 34 and 36 may be used to fill compartments 12 and 14 with solutions A and B, respectively. Following mixture of solutions A and B, port 34 and/or 36 may be used to remove the mixed solution from container 10 for use in the appropriate application. Ports 34 and 36 may include one or more structure (seals, valves, etc.) to control movement of fluid through the ports and to maintain the sterility of the solutions within container 10.

In one embodiment, container 10 may include one or more dedicated input or fill ports and one or more dedicated output ports. The fill ports may be configured and/or positioned to allow the separate components or solutions to be filled into the separate compartments of container 10, and the dedicated output port may be configured and/or positioned such that fluid can be removed from container 10 only after breach of seals 18 and/or 20 have occurred.

As shown in FIG. 3, in one embodiment, container 10 may include dedicated input ports and a dedicated output port. For example, container 10 may include an output port, shown as port 38, that traverses the outer peripheral seal of container 10 adjacent compartment 16 and provides fluid communication with compartment 16. With output port 38 in communication with compartment 16, the solution of container 10 can only be removed if the solution is present in compartment 16. Further, ports 34 and 36 may be configured to ensure that fluid is allowed to flow only one-way into compartments 12 and 14, and port 38 may be configured to permit fluid flow only one-way out of compartment 16. In some embodiments, ports 34 and 36 may include a one-way valve (e.g., a check valve) that allows fluid to flow only into compartments 12 and 14. Port 38 may include a one-way valve (e.g., a check valve) that allows fluid to flow only out of compartment 16 through port 38. The one-way valves in the ports ensure that only ports 34 and 36 may be used for filling container 10 and that only output port 38 can be used to deliver fluid from container 10.

Generally, first and second sheets 22 and 24 may be made of any suitable material such as, for example, a flexible material, and the first sheet 22 may be made of the same or a different material as the second sheet 24. More specifically, the material used for the first and/or second sheets 22 and 24 may vary depending on the fluids to be stored in the first and/or second compartments 12 and 14. In some examples, the first and second sheets 22 and 24 may each include a single layer plastic sheet. Alternatively, in other examples, the first and second sheets 22 and 24 may each include a multilayer plastic sheet. Additionally, the type of material used for the first and/or second sheets 22 and 24 may depend on the method (e.g., heating method, welding method, etc.) used to form seals 18 and 20 and/or the outer peripheral seal of container 10. Some methods of forming peelable seals and/or the outer peripheral seal of container 10 include, for example, direct heat sealing and/or RF sealing. In some examples, the first and second sheets 22 and 24 may be made of a RF-responsive plastic material or RF-responsive resin material to enable RF-welding to be utilized to form the outer peripheral seals 26, 28, 30 and 32 of container 10 and/or frangible seals 18 and 20. Generally, RF-responsive resins are resins that may be heated by RF energy.

In some exemplary embodiments, the first and second sheets 22 and 24 have a thickness between about 1 mil and 10 mils depending on the type of sheets used (e.g., a single plastic sheet or a multilayer plastic sheet). A multilayer sheet may include a plurality of different plastic films adhered to one another to form a single sheet, which has properties not possessed by a single plastic sheet. The first and second sheets 22 and 24 may be made of multilayer sheets if, for example, the fluid to be contained in the first and/or second compartments 12 and/or 14 is only compatible with particular types of materials (e.g., particular types of plastics) and/or the fluid to be contained in the first and/or second compartments 12 and/or 14 requires a material (e.g., plastic) that is substantially impenetrable to air, oxygen and/or moisture.

In other examples, the first and second sheets 22 and 24 may be plastic or polymer sheets and specifically, may be a single layer of polyvinylchloride (PVC) film having a thickness of between about 3 mils and 18 mils. Typically, PVC film is compatible with whole blood as well as blood products and also may be used as a contacting surface for a wide variety of therapeutic solutions. Additionally, the PVC film is RF-responsive (e.g., RF-welding may be utilized to form the outer peripheral seals 26, 28, 30 and 32 of container 10 and/or frangible seals 18 and 20). However, any other suitable material or plastic resin may be utilized to produce the first and/or the second sheets 22 and/or 24 such as, for example, non-PVC materials, non-DEHP materials, polyolefins, polyamides, polyesters, polybutadiene, styrene and hydrocarbon copolymers and mixtures thereof.

In some embodiments, the seals 18 and 20 may be formed by a direct heat sealing method, a RF sealing method or an ultrasonic welding method. To form peelable seals 18 and 20, a sealing die bar may be brought into contact with the outer surface of sheets 22 and/or 24 at the location where seals 18 and 20 are to be formed. The die bar is then energized with, for example, heat energy, RF energy, ultrasonic energy, etc., causing sheets 22 and 24 to melt together to form the desired peelable seal. In one embodiment, peelable seals 18 and 20 may be formed after the outer peripheral seal of container 10 has been formed. In one embodiment, the formation of seals 18 and 20 may include the positioning of a mesh material between sheets 22 and 24 prior to the formation of seals 18 and 20. Use of a mesh material between sheets 22 and 24 may allow for formation of a peelable seal with desirable break or breach characteristics. Various embodiments of container 10 and formation of peelable seals 18 and 20 are disclosed in U.S. Patent Publication No. US 2009/0214807, filed Feb. 24, 2009, which is incorporated herein by reference in its entirety.

While the embodiments of seals 18 and 20 discussed above relate primarily to frangible, peelable seals, formed by melt-sealing together opposing polymer sheets, other suitable sealing structures may be used. For example, seals 18 and 20 may be peelable seals formed by a liquid tight adhesive material. In another exemplary embodiment, seals 18 and 20 may be formed by opposing groove and ridge structures that are configured to releasably interlock to form a fluid tight seal (e.g., a Zip-Loc type sealing structure).

In various embodiments, frangible seals 18 and 20 are seals formed between sheets 22 and 24 that are configured to allow the user or production machinery to break the seals by manipulating container 10 in order to mix together the contents of compartments 12 and 14. For example, seals 18 and 20 may be breached by grasping the outer surfaces of sheets 22 and 24 and applying an outwardly direct force (i.e., a force directed outwardly away from the outer surface of container 10) causing sheets 22 and 24 to separate at seals 18 and 20. In one such embodiment, container 10 may include one or more structures (e.g., grasping tabs) extending from the outer surface of container 10 that facilitates grasping and separation of seals 18 and 20. As another example, seals 18 and 20 may be breached by applying pressure to compartments 12 and 14 such the liquid within compartments 12 and 14 force seals 18 and 20 to rupture.

As mentioned above, container 10 may be used to hold any solution for which it is desirable to provide separation between two components. In one embodiment, solution A and solution B may be components of a therapeutic solution (e.g., a drug solution, nutraceutical solution, blood solution, blood component solution, saline solution, etc.) separated within container 10. For example, solution A and solution B may be components of a platelet storage media or platelet additive solution (PAS) (e.g., PAS 1, PAS 2, PAS 3, PAS 4, PAS 5, etc.), and/or InterSol platelet additive solution offered by Fenwal, Inc. The platelet storage medium is preferably an aqueous storage solution that includes one or more nutrients and buffer(s) in a salt solution. Thus, for example, one of the container compartments (e.g. Solution A) may include a portion of the platelet additive solution, including acetate, citrate, phosphate, potassium and/or bicarbonate, while the other compartment (e.g. Solution B) may include a second portion of the solution, such as glucose, magnesium, calcium, saline and/or other components if desired. Once combined (such as by rupturing one or more of the frangible seals to combine the first and second portions (e.g. Solutions A and B)) the final storage solution preferably includes a mixture of some or all of the above-mentioned components, with the pH of the final storage solution preferably ranging from 6.5-7.5.

In an alternative exemplary embodiment, solution A and solution B may be components a red blood cell preservative or storage solution such as, for example, Adsol, SAG-M and/or ESOL, also offered by Fenwal, Inc. Thus, for example, one of the compartments A or B may include sodium citrate, sodium phosphate, adenine, mannitol and/or sodium chloride and the other of compartments A or B may include at least glucose, along with other components if desired. Once combined (such as by rupturing one or more of the frangible seals to combine the first and second portions of the solution) the final red blood cell storage solution preferably includes a mixture of some or all of the above-mentioned components, with the pH of the final storage solution preferably ranging from 7.4 to 8.4.

It is also contemplated that, in addition to the containers described above in which a blood component storage/preservative solution is contained in first and/or second compartments (which portions may be pre-combined in a single compartment or combined at a later time to form a final additive/storage solution for blood or blood components including platelets and/or RBC), the container may include an additional frangible seal forming an additional compartment that may contain, for example, whole blood or a particular blood component(s). Thus, during use, at least one of the frangible seals may be broken to allow the various solution components to be combined to form a final solution. The additional frangible seal may also be broken to allow the blood or blood component, such as platelets and/or RBCs, to mix with the solution. The breaking of the various frangible seals may be performed simultaneously or in a selected order to allow for mixing of the solution and blood/blood components in a particular sequence.

In other exemplary embodiments, at least one of the compartments, such as first compartment 12 may contain blood or a blood component (e.g., red blood cells, white blood cells, plasma, platelets, combinations thereof, etc.) and another of the multiple compartments, such as the second compartment 14, may contain a treating fluid or treating device (e.g., a pathogen inactivation solution or compound). In other exemplary embodiments, first compartment 12 may contain blood or a blood component and second compartment 14 may contain a preservative solution. Specifically, first compartment 12 may receive red blood cells and second compartment 14 may contain a red blood cell preservative or storage solution such as, for example, Adsol, SAG-M and/or ESOL described above.

In one embodiment, at least one of the compartments, such as first compartment 12 may contain a blood component and second compartment 14 may include a compound absorption device associated with pathogen inactivation. Generally, the compound absorption device associated with pathogen inactivation may substantially remove pathogen inactivation agents, by-products of a pathogen inactivation treatment or even the pathogens themselves.

Figure 4:
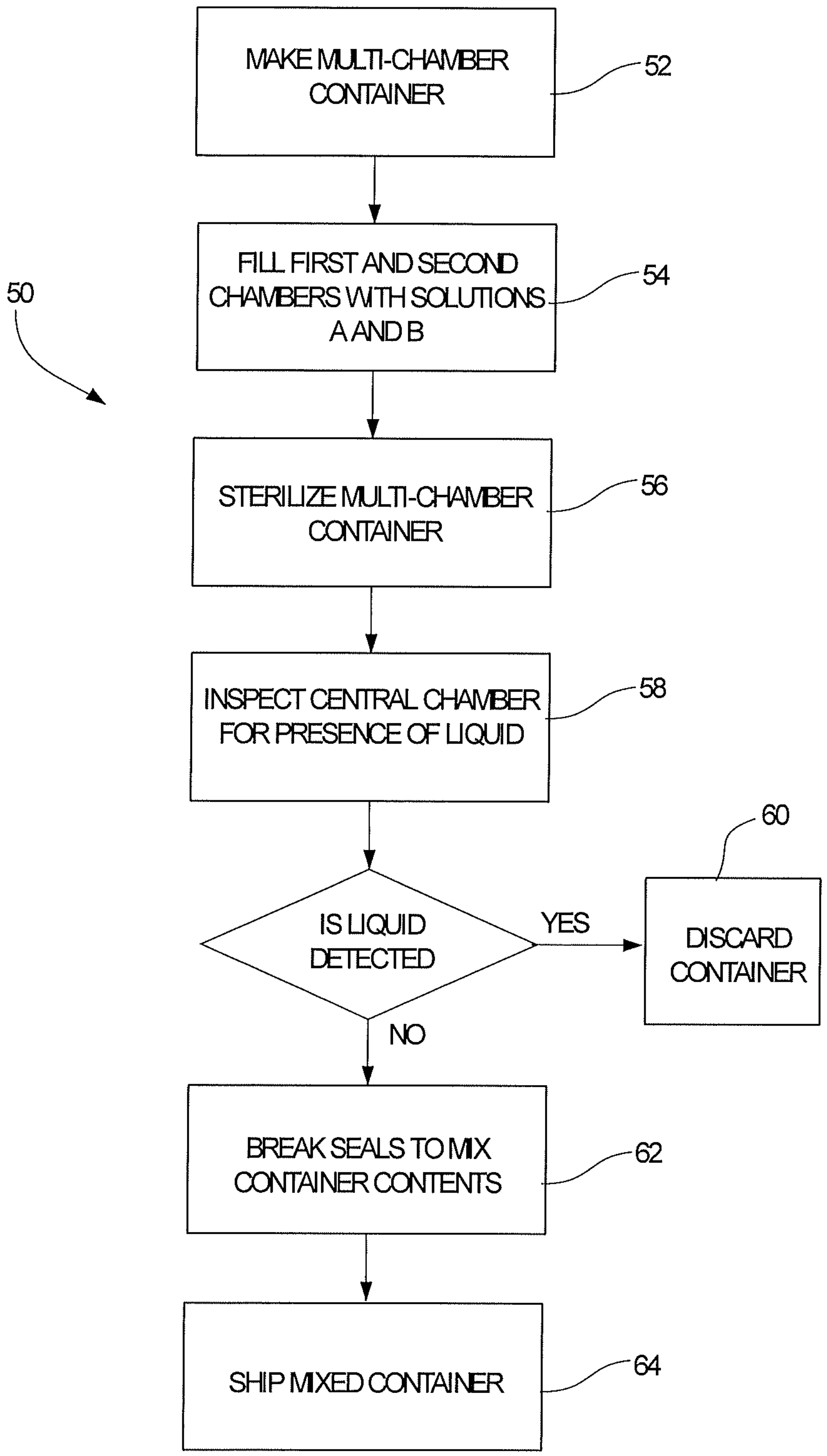
FIG. 4 is a flow-diagram showing the method making a multi-chamber container and fluid combination according to an exemplary embodiment.

Referring to FIG. 4, a method 50 for making container 10 including, for example, a therapeutic substance or one or more solutions is shown according to an exemplary embodiment. At step 52, container 10 is made as discussed above. At step 54, chamber 12 is filed with solution component A and chamber 14 is filled with solution component B. As noted above, solution components A and B may be components of a platelet additive solution or storage media or alternatively, components of a RBC preservation solution. At step 56, container 10 and its contents are sterilized. In one embodiment, container 10 is sterilized by autoclave. At step 58, chamber 16 is inspected to detect whether either seal 18 or seal 20 has broken. In this embodiment, inspection for breakage of seals 18 and 20 occurs following autoclave because solutions A and B, if mixed, may undergo a chemical reaction during the autoclave process. As noted above, the inspection at step 58 may occur via human inspection of the chamber 16 for presence of liquid or via machine inspection of chamber 16 for the presence of liquid. If liquid is detected in chamber 16, the container is discarded at step 60.

If liquid is not detected in chamber 16, it is likely that seals 18 and 20 remained intact before and during autoclave, and then at step 62, seals 18 and 20 are broken allowing solution components A and B to mix. In one embodiment, seals 18 and 20 may be broken manually, and in another embodiment, seals 18 and 20 may be broken utilizing a machine or apparatus to automatically break seals 18 and 20 following inspection of chamber 16 and confirmation that chamber 16 is free from liquid.

In one embodiment, the seal breaking apparatus may grip the outer surfaces of container 10 and apply an outwardly directed force causing seals 18 and 20 to break. In another embodiment, the seal breaking apparatus may press on compartments 12 and 14, causing a localized increase in fluid pressure at seals 18 and 20 that cause the seals to break. In an embodiment in which a manufacturing worker inspects chamber 16, the user may interact with a user input device to indicate whether liquid was detected in chamber 16 at step 58. If the user input indicates that no liquid was detected in chamber 16, a control signal based upon the input received by the user input device is communicated to the seal breaking apparatus, and the seal breaking apparatus breaks seals 18 and 20 in response to the control signal. In an embodiment in which inspection of chamber 16 is completed using a machine inspection system, a control signal is communicated to the seal breaking apparatus if no liquid is detected within chamber 16, and the seal breaking apparatus breaks seals 18 and 20 in response to the control signal. At step 64, container 10 including the mixed solution is shipped to the customer.

Figure 5:
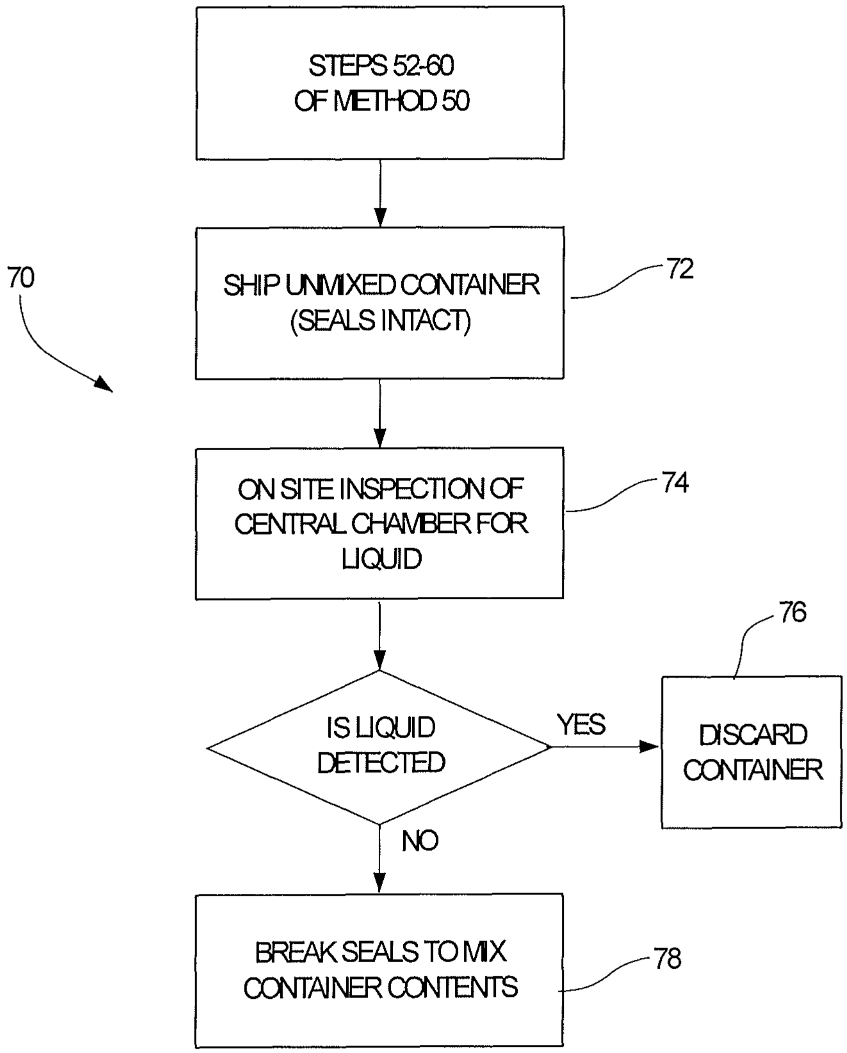
FIG. 5 is a flow-diagram showing a method of making and use of multi-chamber container and fluid combination according to another exemplary embodiment.

Referring to FIG. 5, a method 70 for producing container 10 including a therapeutic substance and/or one or more solutions is shown according to an exemplary embodiment. Method 70 may be practiced for solutions in which it is undesirable to mix solution components A and B more than a short time before use. Steps 52-60 of method 70 are the same as the corresponding steps of method 50. If no liquid is detected within chamber 16, container 10 is shipped to the customer with seals 18 and 20 intact and solution components A and B remaining separated at step 72. At step 74, an on-site or point-of-use inspection of chamber 16 for liquid occurs via one of the inspection processes discussed above. If liquid is detected in chamber 16, the container is discarded at step 76. If liquid is not detected in chamber 16, the container 10 is used at step 78.

It should be understood that the present application is not limited to the details or methodology set forth in the description or illustrated in the figures. It should also be understood that the terminology is for the purpose of description only and should not be regarded as limiting.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

We claim:

1. A container comprising:

opposed first and second sheets sealed along at least a portion of a peripheral edge to define an interior chamber comprising a top edge, a bottom edge and first and second opposing lateral edges, at least first and second frangible seals located in said interior chamber, said first and second seals forming separate first, second and third compartments in said container interior chamber, wherein said third compartment is located between said first and second compartments, said third compartment being defined by said first and second frangible seals and at least a portion of said top and bottom or first and second opposing lateral peripheral edges, wherein said third compartment of said interior chamber is substantially devoid of fluid when said first and second frangible seals are intact and further comprises an indicator associated with said interior chamber and is adapted to detect premature breach of one or both of said at least first and second frangible seals; wherein each of said at least first and second frangible seals are defined by contact between said opposed first and second sheets along the entire length of said seal.

2. The container of claim 1 wherein said container comprises a material selected from the group consisting of PVC materials, non-PVC materials, non-DEHP materials, polyolefins, polyamides, polyesters, polybutadiene, styrene, hydrocarbon copolymers and combinations thereof.

3. The container of claim 1 wherein said first compartment contains a first fluid and said second compartment contains a material different than said first fluid.

4. The container of claim 3 wherein said first fluid comprises a blood component.

5. The container of claim 1 wherein each of said first and second compartments contain a fluid.

6. The container of claim 1 wherein said third compartment comprises a substantially transparent window in at least a portion of one of said first and second container sheets, said window configured to facilitate visual detection of fluid within said third compartment.

7. The container of claim 1 wherein said first and second frangible seals are formed by at least one of: melt-sealing, RF-sealing, ultrasonic sealing, adhesive material and interlocking structures on at least one of said first and second container sheets.

8. The container of claim 1 wherein said indicator comprises a material selected from the group consisting of: a liquid, a gas, a solid, a powdered material and combinations thereof.

9. The container of claim 1 wherein said indicator comprises a color changing material.

10. The container of claim 9 wherein said color changing material comprises a substance responsive to the presence of the contents of at least one of said first and second compartments.

11. The container of claim 10 wherein said color changing material is responsive to at least one of: the presence of fluid, the pH, the ion concentration, a specific molecule and a specific chemical, or combinations thereof, of the contents of at least one of said first and second compartments.

12. The container of claim 1 wherein said indicator is incorporated into at least a portion of at least one of said first and second container sheets.

13. The container of claim 1 wherein at least one of said first and second frangible seals comprises said indicator.

14. The container of claim 1 wherein said container further comprises a port in communication with at least one of said first and second chambers.

15. The container of claim 14 wherein said container further comprises a port in communication with said third chamber.

16. The container of claim 1 further comprising a third frangible seal located in said interior chamber, said first, second and third frangible seals forming separate first, second, third and fourth compartments in said container interior chamber.

17. The container of claim 16 wherein said first compartment contains a first material, said second compartment contains a material different than said first material, and at least one of said third and fourth compartments contains a material different than the material contained in said first and second compartments.

18. The container of claim 16 wherein at least one of said first, second, third and fourth compartments contains at least one of a blood component and an additive solution.

19. The container of claim 18 wherein at least one of said first, second, third and fourth compartments contains an first indicator adapted to detect premature breach of at least one of said first, second and third frangible seals.

20. The container of claim 19 wherein another of said first, second, third and fourth compartments contains a second indicator adapted to detect premature breach of at least one of said first, second and third frangible seals.

21. The container of claim 20 wherein said first and second indicators are the same.

22. The container of claim 20 wherein said first and second indicators are different.

23. The container of claim 1 wherein said indicator comprises a material or device to detect said breach.

24. The container of claim 1 wherein said indicator comprises a machine vision system.

25. A method of forming a container having a seal breach detection indicator comprising:

sealing first and second opposing sheets at their peripheral edges to form an interior chamber comprising a top edge, a bottom edge and first and second opposing lateral edges, forming at least first and second frangible seals between said first and second opposing sheets to define first, second and third compartments in said interior chamber, wherein said third compartment is located between said first and second compartments, said third compartment being defined by said at least first and second frangible seals and at least a portion of said top and bottom or first and second opposed lateral peripheral edges, filling said first chamber with a first solution and filling said second chamber with a second solution, providing an indicator within said interior chamber to detect premature breach of one or both of said first and second frangible seals, detecting the presence of at least one of said first and second solutions in said third compartment to determine premature breach of at least one of said first and second frangible seals; wherein each of said at least first and second frangible seals are defined by contact between said opposed first and second sheets along the entire length of said seal.

26. The method of claim 25 further comprising providing an indicator material in said third compartment adapted to detect premature breach of one or both of said first and second frangible seals.

27. The method of claim 25 comprising providing said indicator in at least one of said first or second frangible seals.

28. The method of claim 25 comprising providing said indicator within said third compartment.

29. The method of claim 25 comprising providing said indicator in at least one of said opposing sheets.

* * * * *